United States Patent
Menn

(10) Patent No.: US 9,642,626 B2
(45) Date of Patent: May 9, 2017

(54) TRANSCEND SURGICAL CLIPS FOR LAPROSCOPIC PROCEDURES

(71) Applicant: Conmed Corporation, Utica, NY (US)

(72) Inventor: Pavel Menn, Marblehead, MA (US)

(73) Assignee: CONMED CORPORATION, Utica, NY (US)

(*) Notice: Subject to any disclaimer, the term of this patent is extended or adjusted under 35 U.S.C. 154(b) by 386 days.

(21) Appl. No.: 14/171,759

(22) Filed: Feb. 3, 2014

(65) Prior Publication Data

US 2014/0222041 A1    Aug. 7, 2014

Related U.S. Application Data

(60) Provisional application No. 61/759,463, filed on Feb. 1, 2013.

(51) Int. Cl.
| | |
|---|---|
| *A61B 17/08* | (2006.01) |
| *A61B 17/122* | (2006.01) |
| *A61B 17/12* | (2006.01) |
| *A61B 17/00* | (2006.01) |

(52) U.S. Cl.
CPC ............ *A61B 17/122* (2013.01); *A61B 17/08* (2013.01); *A61B 17/083* (2013.01); *A61B 17/12* (2013.01); *A61B 2017/00778* (2013.01)

(58) Field of Classification Search
CPC ..... A61B 17/122; A61B 17/08; A61B 17/083; A61B 17/12
See application file for complete search history.

(56) References Cited

U.S. PATENT DOCUMENTS 6,193,732 B1* 2/2001 Frantzen ............ A61B 17/1227
606/151

* cited by examiner

*Primary Examiner* — Gregory Anderson
(74) *Attorney, Agent, or Firm* — Frederick J.M. Price; Bond, Schoeneck & King, PLLC

(57) ABSTRACT

A surgical clip for a clip applier to ligate vessels. The clip contains two opposing external and internal legs connected in parallel by two external apex and one internal apex to form a Y-shape configuration. As a vessel is ligated and compressed between the two external legs, the vessel attempting to expand from its compressed position, applies outwardly lateral forces to the external legs causing them to rotate outwardly. In response, the two opposing internal legs rotate in an opposing directions to the external legs rotations to maintain the position of the clip over the compressed tubular vessel.

14 Claims, 7 Drawing Sheets

TRANSCEND SURGICAL CLIPS FOR LAPROSCOPIC PROCEDURES

CROSS REFERENCE TO RELATED APPLICATION

This application claims the benefit of U.S. Provisional Patent Application No. 61/759,463, filed on Feb. 1, 2013, the contents of which are incorporated herein by reference.

FIELD OF THE INVENTION

This invention relates to novel surgical ligation clips for ligating blood vessels during laparoscopic or endoscopic procedures.

BACKGROUND OF INVENTION

In order to operate on a given tissue or a blood vessel, surgeons must ligate or occlude nearby blood vessels to prevent patient blood loss. Surgeons employ small surgical clips and long cartridges within the clip appliers to ligate or occlude blood vessels in laparoscopic and endoscopic surgical procedures. These surgical clips need to perform multiple functions.

First, the surgical clip must be securely located on the blood vessel. Movement or slippage of the surgical clip on the vessel should be minimized or eliminated once the clip has been applied. Second, the surgical clip should completely close the blood vessel to which it is applied. Movement or slippage of the surgical clip or failure to fully close a blood vessel may cause one or more of the following: damage to nearby tissue, interference on the surgical site, patient blood loss, a lethal drop in blood pressure, or loss of the clip inside the patient. Third, the surgical clip should be designed to minimize damage to the closed blood vessel and surrounding tissue as much as possible. Surgical clips that cause tissue or blood vessel damage may result in internal bleeding, a lethal drop in blood pressure, infections, or longer recovery periods.

Examples of surgical clips are described in U.S. Pat. Nos. 6,610,073; 6,217,590; 5,509,920; 5,501,693; 5,201,746; 5,171,253; 5,171,252; 5,100,420; 5,084,057; 5,026,382; 4,971,198; 4,976,722; 4,979,950; 4,844,066; 4,799,481; 4,702,247; 4,414,721; 4,188,953; 4,146,130; 3,867,944; and 3,363,628; and U.S. Published Patent Application Nos. 2007/0173866; 2005/0273122; and 2004/0153107; all of which are herein incorporated by reference in their entirety.

Previously disclosed surgical clips have two surgical legs defined by a pair of legs joined at a proximal end by an apex and spaced apart at a distal end to define a space between the legs. A clip applier places a surgical clip over a blood vessel within this space and releases the spring loaded legs to ligate the vessel.

However, the previously disclosed surgical clips have legs that do not close or open in directions that are substantially parallel to each other. Non-parallel closure over a vessel leads to clip slippage on the vessel.

Thus, the previously disclosed surgical clips are not adequately secured on blood vessel Accordingly, the subject invention is a novel surgical clip with two legs that close in a substantially parallel way, with less dependence on the position and size of the tissue occluded, thereby securely fastening to and closing a blood vessel while minimizing slippage and damage to the vessel.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting The subject invention discloses a surgical clip, comprising: a relatively non-deformable first elongated external leg member extending along a first leg axis from a first proximal end to a first distal end, a relatively non-deformable first elongated internal leg member extending along the first leg axis from the first distal end to a first middle end, a relatively deformable first external apex member coupling the proximal end of the first elongated external leg member and the first elongated internal leg member whereby the first elongated external leg member and the first elongated internal leg member are substantially coplanar, further wherein the first elongated external leg member and the first elongated internal leg member have an external surface and an inner surface extending along the first leg axis, and have a cross-section transverse to the first leg axis and defined by a substantially curved boundary component; a relatively non-deformable second elongated external leg member extending along a second leg axis from a second proximal end to a second distal end, a relatively non-deformable second elongated internal leg member extending along the second external leg axis from the second distal end to a second middle end, a relatively deformable second external apex member coupling the proximal end of the second elongated external leg member and the second elongated internal leg member whereby the second elongated external leg member and the second elongated internal leg member are substantially coplanar, further wherein the second elongated external leg member and the second elongated internal leg member have an external surface extending and an inner surface along the second leg axis, and have a cross-section transverse to the second leg axis and defined by a substantially curved boundary component; and a relatively deformable internal apex member coupling the first middle end of the first elongated internal leg member with the second middle end of the second elongated internal leg member whereby the first leg axis and the second leg axis are substantially coplanar and substantially parallel and extend along a clip axis, whereby the first elongated internal leg member is opposite the second elongated internal leg member, further wherein the first elongated external leg member is opposite the second elongated external leg member.

The subject invention also discloses a surgical clip, comprising: a first elongated external leg member extending along a first leg axis from a first proximal end to a first distal end, a first elongated internal leg member extending along the first leg axis from the first distal end to a first middle end, a first external apex member coupling the proximal end of the first elongated external leg member and the first elongated internal leg member whereby the first elongated external leg member and the first elongated internal leg member are substantially coplanar, further wherein the first elongated external leg member and the first elongated internal leg member have an external surface and an inner surface extending along the first leg axis, and have a cross-section transverse to the first leg axis and defined by a substantially curved boundary component; a second elongated external leg member extending along a second leg axis from a second proximal end to a second distal end, a second elongated internal leg member extending along the second external leg axis from the second distal end to a second middle end, a second external apex member coupling the proximal end of the second elongated external leg member and the second elongated internal leg member whereby the second elongated external leg member and the second elongated internal leg member are substantially coplanar, further wherein the second elongated external leg member and the second elongated internal leg member have an external surface extending and an inner surface along the second leg axis, and have a cross-section transverse to the second leg axis and defined by a substantially curved boundary component; and an internal apex member coupling the first middle end of the first elongated internal leg member with the second middle end of the second elongated internal leg member whereby the first leg axis and the second leg axis are substantially coplanar and substantially parallel and extend along a clip axis, whereby the first elongated internal leg member is opposite the second elongated internal leg member, further wherein the first elongated external leg member is opposite the second elongated external leg member.

In further embodiments of the subject invention, a compressed vessel is placed between the inner lateral surfaces of the first elongated external leg member and the second elongated external leg member, wherein the vessel applies uncompressing forces to the inner lateral surfaces of first elongated external leg member and the second elongated external leg member, further wherein the uncompressing forces cause a first rotation of the first elongated external leg member at the first external apex away from the first elongated internal leg member and the clip axis, and a second rotation of the second elongated external leg member at the second external apex away from the second elongated internal leg member and the clip axis, wherein the first elongated internal leg member applies a third rotation at the internal apex member, wherein the third rotation substantially opposes the first rotation to substantially maintain the first elongated external leg member in the clip axis and compressed over the vessel, wherein the second elongated internal leg member applies a fourth rotation at the internal apex member, wherein the fourth rotation substantially opposes the second rotation to substantially maintain the second elongated external leg member in the clip axis and compressed over the vessel.

In further embodiments of the subject invention, a compressed vessel is placed between the inner lateral surfaces of the first elongated external leg member and the second elongated external leg member, wherein the vessel generates forces in substantially lateral directions to the inner lateral surfaces of first elongated external leg member and the second elongated external leg member, further wherein the lateral forces push the first elongated external leg member into a first rotation at the first external apex away from the first elongated internal leg member and the clip axis, and push the second elongated external leg member into a second rotation at the second external apex away from the second elongated internal leg member and the clip axis, wherein the first elongated internal leg member generates a third rotation at the internal apex member, wherein the third rotation substantially opposes the first rotation to substantially maintain the first elongated external leg member in the clip axis and compressed over the vessel, wherein the second elongated internal leg member generates a fourth rotation at the internal apex member, wherein the fourth rotation substantially opposes the second rotation to substantially maintain the second elongated external leg member in the clip axis and compressed over the vessel.

In other embodiments of the subject invention, a compressed vessel is positioned between the inner lateral surfaces of the first elongated external leg member and the second elongated external leg member, wherein the vessel generates tension in substantially lateral directions to the inner lateral surfaces of first elongated external leg member and the second elongated external leg member, further wherein the lateral tension pushes the first elongated external leg member into a first rotational tension at the first external apex away from the first elongated internal leg member and the clip axis, and pushes the second elongated external leg member into a second rotational tension at the second external apex away from the second elongated internal leg member and the clip axis, wherein the first elongated internal leg member generates a third rotational tension at the internal apex member, wherein the third rotational tension substantially opposes the first rotational tension to substantially maintain the first elongated external leg member in the clip axis and compressed over the vessel, wherein the second elongated internal leg member generates a fourth rotational tension at the internal apex member, wherein the fourth rotational tension substantially opposes the second rotational tension to substantially maintain the second elongated external leg member in the clip axis and compressed over the vessel.

In other embodiments of the subject invention, a compressed vessel is positioned between the inner lateral surfaces of the first elongated external leg member and the second elongated external leg member, wherein the vessel generates a moment of force in substantially lateral directions to the inner lateral surfaces of first elongated external leg member and the second elongated external leg member, further wherein the lateral moment of force drives the first elongated external leg member into a first rotational moment of force at the first external apex away from the first elongated internal leg member and the clip axis, and drives the second elongated external leg member into a second rotational moment of force at the second external apex away from the second elongated internal leg member and the clip axis, wherein the first elongated internal leg member generates a third rotational moment of force at the internal apex member, wherein the third rotational moment of force substantially opposes the first rotational moment of force to substantially maintain the first elongated external leg member in the clip axis and compressed over the vessel, wherein the second elongated internal leg member generates a fourth rotational moment of force at the internal apex member, wherein the fourth rotational moment of force substantially opposes the second rotational moment of force to substantially maintain the second elongated external leg member in the clip axis and compressed over the vessel.

In other embodiments of the subject invention, a compressed vessel is positioned between the inner lateral surfaces of the first elongated external leg member and the second elongated external leg member, wherein the vessel generates pressure in substantially lateral directions to the inner lateral surfaces of first elongated external leg member and the second elongated external leg member, further wherein the lateral pressure drives the first elongated external leg member into a first rotational torque at the first external apex away from the first elongated internal leg member and the clip axis, and drive the second elongated external leg member into a second rotational torque at the second external apex away from the second elongated internal leg member and the clip axis, wherein the first elongated internal leg member generates a third rotational torque at the internal apex member, wherein the third rotational torque substantially opposes the first rotational torque to substantially maintain the first elongated external leg member in the clip axis and compressed over the vessel, wherein the second elongated internal leg member generates a fourth rotational torque at the internal apex member, wherein the fourth rotational torque substantially opposes the second rotational torque to substantially maintain the second elongated external leg member in the clip axis and compressed over the vessel.

The subject invention also discloses a surgical clip, comprising: a relatively non-deformable first elongated external leg member extending along a first leg axis from a first proximal end to a first distal end, a relatively non-deformable first elongated internal leg member extending along the first leg axis from the first distal end to a first middle end, a relatively deformable first external pivot member coupling the proximal end of the first elongated external leg member and the first elongated internal leg member whereby the first elongated external leg member and the first elongated internal leg member are substantially coplanar, further wherein the first elongated external leg member and the first elongated internal leg member have an external surface and an inner surface extending along the first leg axis, and have a cross-section transverse to the first leg axis and defined by a substantially curved boundary component; a relatively non-deformable second elongated external leg member extending along a second leg axis from a second proximal end to a second distal end, a relatively non-deformable second elongated internal leg member extending along the second external leg axis from the second distal end to a second middle end, a relatively deformable second external pivot member coupling the proximal end of the second elongated external leg member and the second elongated internal leg member whereby the second elongated external leg member and the second elongated internal leg member are substantially coplanar, further wherein the second elongated external leg member and the second elongated internal leg member have an external surface extending and an inner surface along the second leg axis, and have a cross-section transverse to the second leg axis and defined by a substantially curved boundary component; and a relatively deformable internal pivot member coupling the first middle end of the first elongated internal leg member with the second middle end of the second elongated internal leg member whereby the first leg axis and the second leg axis are substantially coplanar and substantially parallel and extend along a clip axis, whereby the first elongated internal leg member is opposite the second elongated internal leg member, further wherein the first elongated external leg member is opposite the second elongated external leg member.

The subject invention further discloses a surgical clip, comprising: a first elongated external leg member extending along a first leg axis from a first proximal end to a first distal end, a first elongated internal leg member extending along the first leg axis from the first distal end to a first middle end, a first external pivot member coupling the proximal end of the first elongated external leg member and the first elongated internal leg member whereby the first elongated external leg member and the first elongated internal leg member are substantially coplanar, further wherein the first elongated external leg member and the first elongated internal leg member have an external surface and an inner surface extending along the first leg axis, and have a cross-section transverse to the first leg axis and defined by a substantially curved boundary component; a second elongated external leg member extending along a second leg axis from a second proximal end to a second distal end, a second elongated internal leg member extending along the second external leg axis from the second distal end to a second middle end, a second external pivot member coupling the proximal end of the second elongated external leg member and the second elongated internal leg member whereby the second elongated external leg member and the second elongated internal leg member are substantially coplanar, further wherein the second elongated external leg member and the second elongated internal leg member have an external surface extending and an inner surface along the second leg axis, and have a cross-section transverse to the second leg axis and defined by a substantially curved boundary component; and a internal pivot member coupling the first middle end of the first elongated internal leg member with the second middle end of the second elongated internal leg member whereby the first leg axis and the second leg axis are substantially coplanar and substantially parallel and extend along a clip axis, whereby the first elongated internal leg member is opposite the second elongated internal leg member, further wherein the first elongated external leg member is opposite the second elongated external leg member.

In further embodiments of the subject invention, a compressed vessel is placed between the inner lateral surfaces of the first elongated external leg member and the second elongated external leg member, wherein the vessel applies uncompressing forces to the inner lateral surfaces of first elongated external leg member and the second elongated external leg member, further wherein the uncompressing forces cause a first rotation of the first elongated external leg member at the first external pivot away from the first elongated internal leg member and the clip axis, and a second rotation of the second elongated external leg member at the second external pivot away from the second elongated internal leg member and the clip axis, wherein the first elongated internal leg member applies a third rotation at the internal pivot member, wherein the third rotation substantially opposes the first rotation to substantially maintain the first elongated external leg member in the clip axis and compressed over the vessel, wherein the second elongated internal leg member applies a fourth rotation at the internal pivot member, wherein the fourth rotation substantially opposes the second rotation to substantially maintain the second elongated external leg member in the clip axis and compressed over the vessel.

In further embodiments of the subject invention, a compressed vessel is placed between the inner lateral surfaces of the first elongated external leg member and the second elongated external leg member, wherein the vessel generates forces in substantially lateral directions to the inner lateral surfaces of first elongated external leg member and the second elongated external leg member, further wherein the lateral forces push the first elongated external leg member into a first rotation at the first external pivot away from the first elongated internal leg member and the clip axis, and pushes the second elongated external leg member into a second rotation at the second external pivot away from the second elongated internal leg member and the clip axis, wherein the first elongated internal leg member generates a third rotation at the internal pivot member, wherein the third rotation substantially opposes the first rotation to substantially maintain the first elongated external leg member in the clip axis and compressed over the vessel, wherein the second elongated internal leg member generates a fourth rotation at the internal pivot member, wherein the fourth rotation substantially opposes the second rotation to substantially maintain the second elongated external leg member in the clip axis and compressed over the vessel.

In other embodiments of the subject invention, a compressed vessel is positioned between the inner lateral surfaces of the first elongated external leg member and the second elongated external leg member, wherein the vessel generates tension in substantially lateral directions to the inner lateral surfaces of first elongated external leg member and the second elongated external leg member, further wherein the lateral tension pushes the first elongated external leg member into a first rotational tension at the first external pivot away from the first elongated internal leg member and the clip axis, and pushes the second elongated external leg member into a second rotational tension at the second external pivot away from the second elongated internal leg member and the clip axis, wherein the first elongated internal leg member generates a third rotational tension at the internal pivot member, wherein the third rotational tension substantially opposes the first rotational tension to substantially maintain the first elongated external leg member in the clip axis and compressed over the vessel, wherein the second elongated internal leg member generates a fourth rotational tension at the internal pivot member, wherein the fourth rotational tension substantially opposes the second rotational tension to substantially maintain the second elongated external leg member in the clip axis and compressed over the vessel.

In other embodiments of the subject invention, a compressed vessel is positioned between the inner lateral surfaces of the first elongated external leg member and the second elongated external leg member, wherein the vessel generates a moment of force in substantially lateral directions to the inner lateral surfaces of first elongated external leg member and the second elongated external leg member, further wherein the lateral moment of force drives the first elongated external leg member into a first rotational moment of force at the first external pivot away from the first elongated internal leg member and the clip axis, and drives the second elongated external leg member into a second rotational moment of force at the second external pivot away from the second elongated internal leg member and the clip axis, wherein the first elongated internal leg member generates a third rotational moment of force at the internal pivot member, wherein the third rotational moment of force substantially opposes the first rotational moment of force to substantially maintain the first elongated external leg member in the clip axis and compressed over the vessel, wherein the second elongated internal leg member generates a fourth rotational moment of force at the internal pivot member, wherein the fourth rotational moment of force substantially opposes the second rotational moment of force to substantially maintain the second elongated external leg member in the clip axis and compressed over the vessel.

In other embodiments of the subject invention, a compressed vessel is positioned between the inner lateral surfaces of the first elongated external leg member and the second elongated external leg member, wherein the vessel generates pressure in substantially lateral directions to the inner lateral surfaces of first elongated external leg member and the second elongated external leg member, further wherein the lateral pressure drives the first elongated external leg member into a first rotational torque at the first external pivot away from the first elongated internal leg member and the clip axis, and drive the second elongated external leg member into a second rotational torque at the second external pivot away from the second elongated internal leg member and the clip axis, wherein the first elongated internal leg member generates a third rotational torque at the internal pivot member, wherein the third rotational torque substantially opposes the first rotational torque to substantially maintain the first elongated external leg member in the clip axis and compressed over the vessel, wherein the second elongated internal leg member generates a fourth rotational torque at the internal pivot member, wherein the fourth rotational torque substantially opposes the second rotational torque to substantially maintain the second elongated external leg member in the clip axis and compressed over the vessel.

In additional embodiments of the subject invention, the third rotation substantially opposes the first rotation, and the fourth rotation substantially opposes the second rotation to substantially maintain the first and second elongated external leg members in a substantially parallel position with each other over the compressed vessel. In further embodiments of the subject invention, the first and third rotations are substantially coplanar, and the second and fourth rotations are substantially coplanar.

In additional embodiments of the subject invention, the third rotational tension substantially opposes the first rotational tension, and the fourth rotational tension substantially opposes the second rotational tension to substantially maintain the first and second elongated external leg members in a substantially parallel position with each other over the compressed vessel. In further embodiments of the subject invention, the first and third rotational tensions are substantially coplanar, and the second and fourth rotational tensions are substantially coplanar.

In additional embodiments of the subject invention, the third rotational moment of force substantially opposes the first rotational moment of force, and the fourth rotational moment of force substantially opposes the second rotational moment of force to substantially maintain the first and second elongated external leg members in a substantially parallel position with each other over the compressed vessel. In further embodiments of the subject invention, the first and third rotational moment of forces are substantially coplanar, and the second and fourth rotational moment of forces are substantially coplanar.

In additional embodiments of the subject invention, the third rotational torque substantially opposes the first rotational torque, and the fourth rotational torque substantially opposes the second rotational torque to substantially maintain the first and second elongated external leg members in a substantially parallel position with each other over the compressed vessel. In further embodiments of the subject invention, the first and third rotational torques are substantially coplanar, and the second and fourth rotational torques are substantially coplanar.

In a further embodiment of the subject invention, the first external leg member, the first internal leg member, the second external leg member, and the second internal leg member may each have a substantially variable width transverse to the respective first leg axis and second leg axis.

In another embodiment of the subject invention, the first external leg member, the first internal leg member, the second external leg member, and the second internal leg member may each have a substantially variable shapes transverse to the respective first leg axis and second leg axis.

In another embodiment of the subject invention, the first external leg member, the first internal leg member, the second external leg member, and the second internal leg member may have a substantially uniform width transverse to the respective first leg axis and second leg axis.

In another embodiment of the subject invention, the first leg axis and the second leg axis may be substantially parallel, and substantially parallel to the clip axis.

In another embodiment of the subject invention, the first external leg member, the first internal leg member, the second external leg member, and the second internal leg member may each comprise a substantially non-textured external surface and inner surface.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external apex coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external apex coupling the third proximal end of the second external leg and the second internal leg whereby the second external leg and the second internal leg are substantially coplanar; and an internal apex coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein uncompressing forces from the compressed vessel causes the first and second external legs to rotate at the first and second external apex away from the first and second internal legs, wherein the first and second internal legs rotate at the internal apex to substantially oppose the rotation of the first and second external legs to maintain the first and second external legs in a substantially parallel position.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external apex coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external apex coupling the third proximal end of the second external leg and the second internal leg whereby the second external leg and the second internal leg are substantially coplanar; and an internal apex coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein the compressed vessel generates tension to push the first and second external legs into rotational tensions at the first and second external apex away from the first and second internal legs, wherein the first and second internal legs generate opposing rotational tensions at the internal apex to substantially oppose the rotational tensions of the first and second external legs to maintain the first and second external legs in a substantially parallel position.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external apex coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external apex coupling the third proximal end of the second external leg and the second internal leg whereby the second external leg and the second internal leg are substantially coplanar; and an internal apex coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein the compressed vessel generates a moment of force to push the first and second external legs into rotational moments of force at the first and second external apex away from the first and second internal legs, wherein the first and second internal legs generate opposing rotational moments of force at the internal apex to substantially oppose the rotational moments of force of the first and second external legs to maintain the first and second external legs in a substantially parallel position.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external apex coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external apex coupling the third proximal end of the second external leg and the second internal leg whereby the second external leg and the second internal leg are substantially coplanar; and an internal apex coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein the compressed vessel generates tension to push the first and second external legs into rotational torques at the first and second external apex away from the first and second internal legs, wherein the first and second internal legs generate opposing rotational torques at the internal apex to substantially oppose the rotational torques of the first and second external legs to maintain the first and second external legs in a substantially parallel position.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external pivot coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external pivot coupling the third proximal end of the second external leg and the second internal leg whereby the second external leg and the second internal leg are substantially coplanar; and an internal pivot coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein uncompressing forces from the compressed vessel causes the first and second external legs to rotate at the first and second external pivot away from the first and second internal legs, wherein the first and second internal legs rotate at the internal pivot to substantially oppose the rotation of the first and second external legs to maintain the first and second external legs in a substantially parallel position.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external pivot coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external pivot coupling the third proximal end of the second external leg and the second internal leg whereby the second external leg and the second internal leg are substantially coplanar; and an internal pivot coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein the compressed vessel generates tension to push the first and second external legs into rotational tensions at the first and second external pivot away from the first and second internal legs, wherein the first and second internal legs generate opposing rotational tensions at the internal pivot to substantially oppose the rotational tensions of the first and second external legs to maintain the first and second external legs in a substantially parallel position.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external pivot coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external pivot coupling the third proximal end of the second external leg and the second internal leg whereby the second external leg and the second internal leg are substantially coplanar; and an internal pivot coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein the compressed vessel generates a moment of force to push the first and second external legs into rotational moments of force at the first and second external pivot away from the first and second internal legs, wherein the first and second internal legs generate opposing rotational moments of force at the internal pivot to substantially oppose the rotational moments of force of the first and second external legs to maintain the first and second external legs in a substantially parallel position.

The subject invention discloses a surgical clip, comprising: a first elongated leg comprising a first external leg extending along a first leg axis from a first proximal end to a first distal end, and a first internal leg extending along a second leg axis from the first proximal end to a second distal end, a first external pivot coupling the first proximal end of the first external leg and the first internal leg whereby the first external leg and the first internal leg are substantially coplanar; a second elongated leg comprising a second external leg extending along a third leg axis from a second proximal end to a third distal end, and a second internal leg extending along a fourth leg axis from the second proximal end to a fourth distal end, a second external pivot coupling the third proximal end of the second external leg and the second internal leg whereby the second external leg and the second internal leg are substantially coplanar; and an internal pivot coupling the second distal end of the first internal leg with the fourth distal end of the second internal leg whereby the first leg axis and the second leg axis are substantially coplanar and substantially parallel and extend along a clip axis, whereby the first internal leg is opposite the second internal leg, further wherein the first external leg is opposite the second external leg, wherein a compressed vessel is placed between inner surfaces of the first external leg and the second external leg, wherein the compressed vessel generates tension to push the first and second external legs into rotational torques at the first and second external pivot away from the first and second internal legs, wherein the first and second internal legs generate opposing rotational torques at the internal pivot to substantially oppose the rotational torques of the first and second external legs to maintain the first and second external legs in a substantially parallel position.

In a further embodiment of the subject invention, the first external leg and second external leg may each have a substantially variable width transverse to the respective first leg axis and third leg axis.

In another embodiment of the subject invention, the first external leg and second external leg may each have a substantially variable shapes transverse to the respective first leg axis and third leg axis.

In another embodiment of the subject invention, the respective first leg and second leg may have a substantially uniform width transverse to the respective first leg axis and third leg axis.

In another embodiment of the subject invention, the first leg axis and the third leg axis may be substantially parallel, and substantially parallel to the clip axis.

In another embodiment of the subject invention, the externals legs and the internal legs may each comprise a substantially non-textured external surface and inner surface.

The subject invention discloses a surgical clip, comprising: two external legs in a substantially parallel position extending along a clip axis from a proximal end to a distal end, two internal legs coupled by two external apex to the proximal ends of each external leg, wherein the distal ends of the two internal legs form an internal central apex, wherein the external legs, the internal legs, the external apex and the internal central apex are all in a substantially coplanar position, wherein a compressed vessel is placed between inner surfaces of the external legs, wherein uncompressing forces from the compressed vessel causes the external legs to rotate at the external apex away from the internal legs and the clip axis, wherein the internal legs rotate at the internal central apex to substantially oppose the rotation of the external legs to maintain the external legs in a substantially parallel position.

The subject invention discloses a surgical clip, comprising: two external legs in a substantially parallel position extending along a clip axis from a proximal end to a distal end, two internal legs coupled by two external apex to the proximal ends of each external leg, wherein the distal ends of the two internal legs form an internal central apex, wherein the external legs, the internal legs, the external apex and the internal central apex are all in a substantially coplanar position, wherein a compressed vessel is placed between inner surfaces of the external legs, wherein the compressed vessel generates tension to push the external legs into rotational tensions at the external apex away from the internal legs and the clip axis, wherein the internal legs generate opposing rotational tensions at the internal central apex to substantially oppose the rotational tensions of the external legs to maintain the external legs in a substantially parallel position.

The subject invention discloses a surgical clip, comprising: two external legs in a substantially parallel position extending along a clip axis from a proximal end to a distal end, two internal legs coupled by two external apex to the proximal ends of each external leg, wherein the distal ends of the two internal legs form an internal central apex, wherein the external legs, the internal legs, the external apex and the internal central apex are all in a substantially coplanar position, wherein a compressed vessel is placed between inner surfaces of the external legs, wherein the compressed vessel generates a moment of force to push the external legs into rotational moments of force at the external apex away from the internal legs and the clip axis, wherein the internal legs generate opposing rotational moments of force at the internal central apex to substantially oppose the rotational moments of force of the external legs to maintain the external legs in a substantially parallel position.

The subject invention discloses a surgical clip, comprising: two external legs in a substantially parallel position extending along a clip axis from a proximal end to a distal end, two internal legs coupled by two external apex to the proximal ends of each external leg, wherein the distal ends of the two internal legs form an internal central apex, wherein the external legs, the internal legs, the external apex and the internal central apex are all in a substantially coplanar position, wherein a compressed vessel is placed between inner surfaces of the external legs, wherein the compressed vessel generates tension to push the external legs into rotational torques at the external apex away from the internal legs and the clip axis, wherein the internal legs generate opposing rotational torques at the internal central apex to substantially oppose the rotational torques of the external legs to maintain the external legs in a substantially parallel position.

The subject invention discloses a surgical clip, comprising: two external legs in a substantially parallel position extending along a clip axis from a proximal end to a distal end, two internal legs coupled by two external pivot to the proximal ends of each external leg, wherein the distal ends of the two internal legs form an internal central pivot, wherein the external legs, the internal legs, the external pivot and the internal central pivot are all in a substantially coplanar position, wherein a compressed vessel is placed between inner surfaces of the external legs, wherein uncompressing forces from the compressed vessel causes the external legs to rotate at the external pivot away from the internal legs and the clip axis, wherein the internal legs rotate at the internal central pivot to substantially oppose the rotation of the external legs to maintain the external legs in a substantially parallel position.

The subject invention discloses a surgical clip, comprising: two external legs in a substantially parallel position extending along a clip axis from a proximal end to a distal end, two internal legs coupled by two external pivot to the proximal ends of each external leg, wherein the distal ends of the two internal legs form an internal central pivot, wherein the external legs, the internal legs, the external pivot and the internal central pivot are all in a substantially coplanar position, wherein a compressed vessel is placed between inner surfaces of the external legs, wherein the compressed vessel generates tension to push the external legs into rotational tensions at the external pivot away from the internal legs and the clip axis, wherein the internal legs generate opposing rotational tensions at the internal central pivot to substantially oppose the rotational tensions of the external legs to maintain the external legs in a substantially parallel position.

The subject invention discloses a surgical clip, comprising: two external legs in a substantially parallel position extending along a clip axis from a proximal end to a distal end, two internal legs coupled by two external pivot to the proximal ends of each external leg, wherein the distal ends of the two internal legs form an internal central pivot, wherein the external legs, the internal legs, the external pivot and the internal central pivot are all in a substantially coplanar position, wherein a compressed vessel is placed between inner surfaces of the external legs, wherein the compressed vessel generates a moment of force to push the external legs into rotational moments of force at the external pivot away from the internal legs and the clip axis, wherein the internal legs generate opposing rotational moments of force at the internal central pivot to substantially oppose the rotational moments of force of the external legs to maintain the external legs in a substantially parallel position.

The subject invention discloses a surgical clip, comprising: two external legs in a substantially parallel position extending along a clip axis from a proximal end to a distal end, two internal legs coupled by two external pivot to the proximal ends of each external leg, wherein the distal ends of the two internal legs form an internal central pivot, wherein the external legs, the internal legs, the external pivot and the internal central pivot are all in a substantially coplanar position, wherein a compressed vessel is placed between inner surfaces of the external legs, wherein the compressed vessel generates tension to push the external legs into rotational torques at the external pivot away from the internal legs and the clip axis, wherein the internal legs generate opposing rotational torques at the internal central pivot to substantially oppose the rotational torques of the external legs to maintain the external legs in a substantially parallel position.

In a further embodiment of the subject invention, the external and internal legs may each have a substantially variable width transverse to the clip axis.

In another embodiment of the subject invention, the external and internal legs may each have a substantially variable shapes transverse to the clip axis.

In another embodiment of the subject invention, the external and internal legs may have a substantially uniform width transverse to the clip axis.

In embodiments of the subject invention, the surgical clip comprises one piece.

In further embodiments of the subject invention, the surgical clip may be 0.1 to 0.5 inches in length.

In embodiments of the subject invention, the surgical clip may be composed of titanium or stainless steel. In further embodiments of the subject invention, the surgical clip may be composed of biodegradable material.

In even further embodiments of the subject invention, there is no minimum vessel closure diameter for the surgical clip.

In other embodiments of the subject invention, the surgical clip may have a substantially Y-shaped configuration.

In embodiments of the subject invention, the term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified.

In embodiments of the subject invention, the term "relatively" is defined as a comparison of a property, or the proportion of a property between two components, the property herein being the deformability between the apex and the legs of the clip.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto. These together with other objects of the invention, along with the various features of novelty, which characterize the invention, are pointed out with particularity in the claims annexed to and forming a part of this disclosure.

BRIEF DESCRIPTION OF THE DRAWINGS

Advantages of the present invention will be apparent from the following detailed description of embodiments thereof, which description should be considered in conjunction with the accompanying drawings, in which.

DETAILED DESCRIPTION OF THE EMBODIMENTS

While several variations of the present invention have been illustrated by way of example in particular embodiments, it is apparent that further embodiments could be developed within the spirit and scope of the present invention, or the inventive concept thereof. However, it is to be expressly understood that such modifications and adaptations are within the spirit and scope of the present invention, and are inclusive, but not limited to the following appended claims as set forth.

The subject invention comprises a transcend ligating clip 1, as shown in FIGS. 1-7. In one embodiment of the subject invention, the clip 1 may have a substantially Y-shaped configuration.

Figure 1:
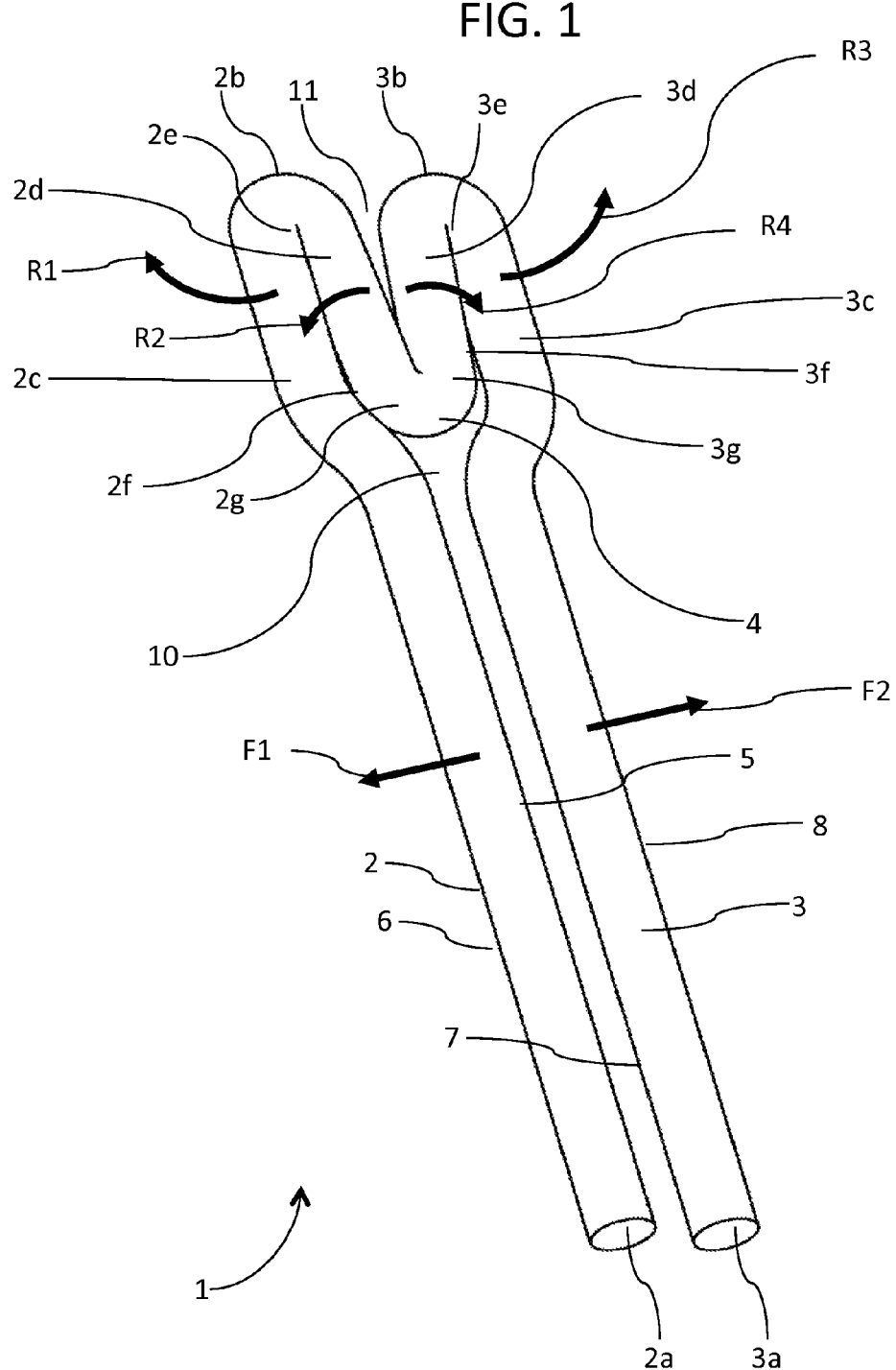
FIG. 1 illustrates a perspective view of one embodiment of a transcend ligating clip in an open position.
Figure 2:
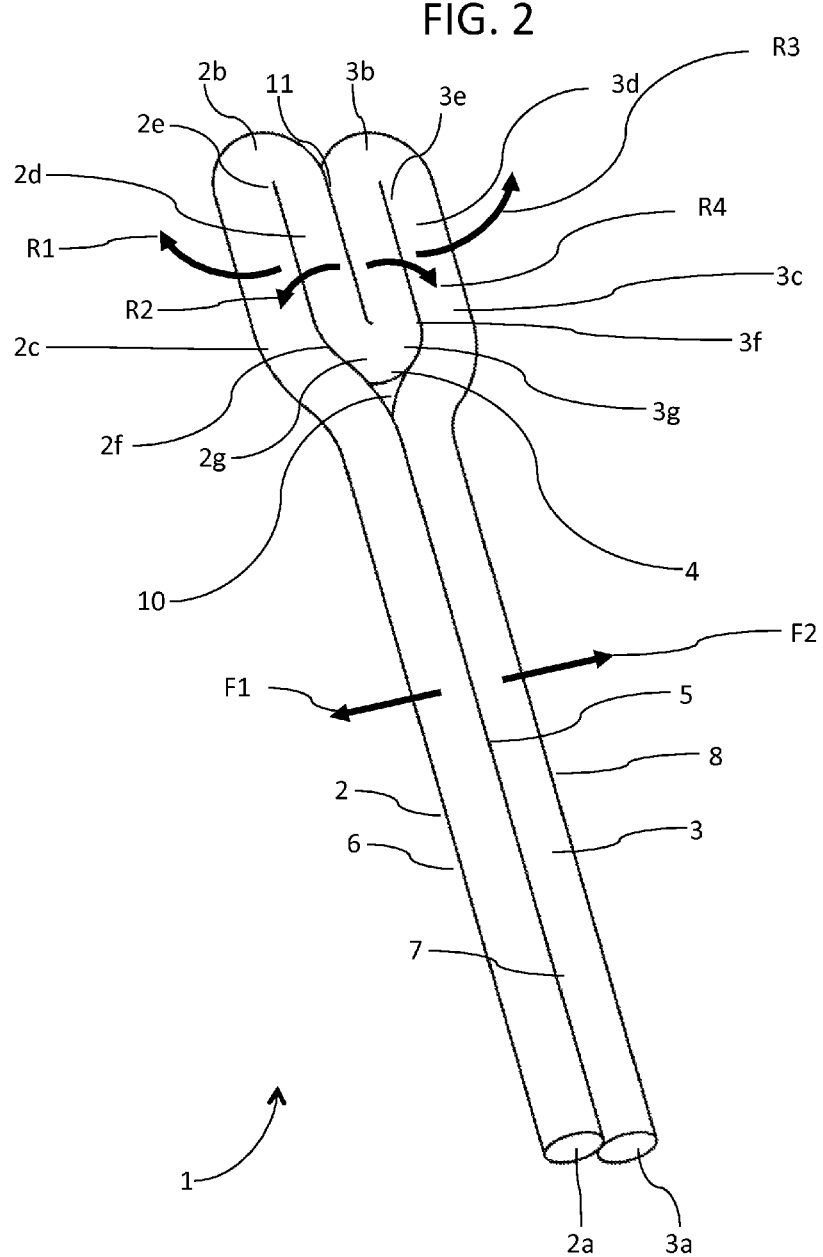
FIG. 2 illustrates a perspective view of the embodiment of the transcend ligating clip in a closed position.
Figure 3:
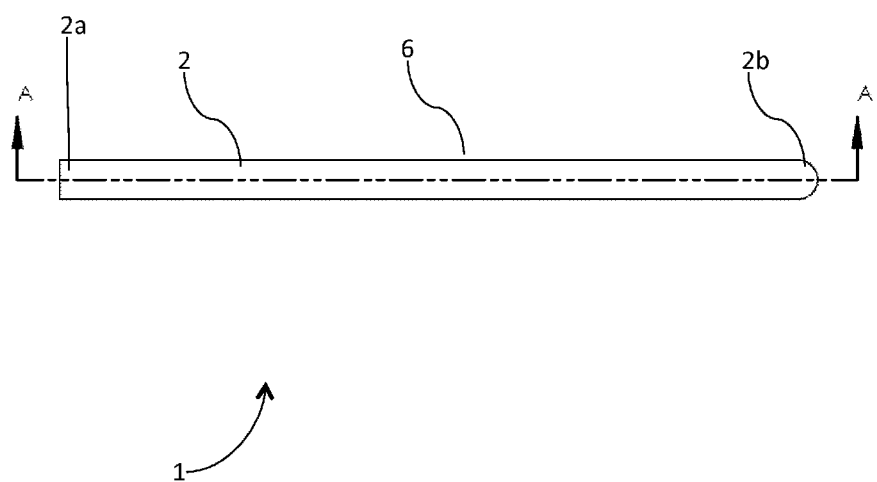
FIG. 3 illustrates a side view of the embodiment of the transcend ligating clip.
Figure 4:
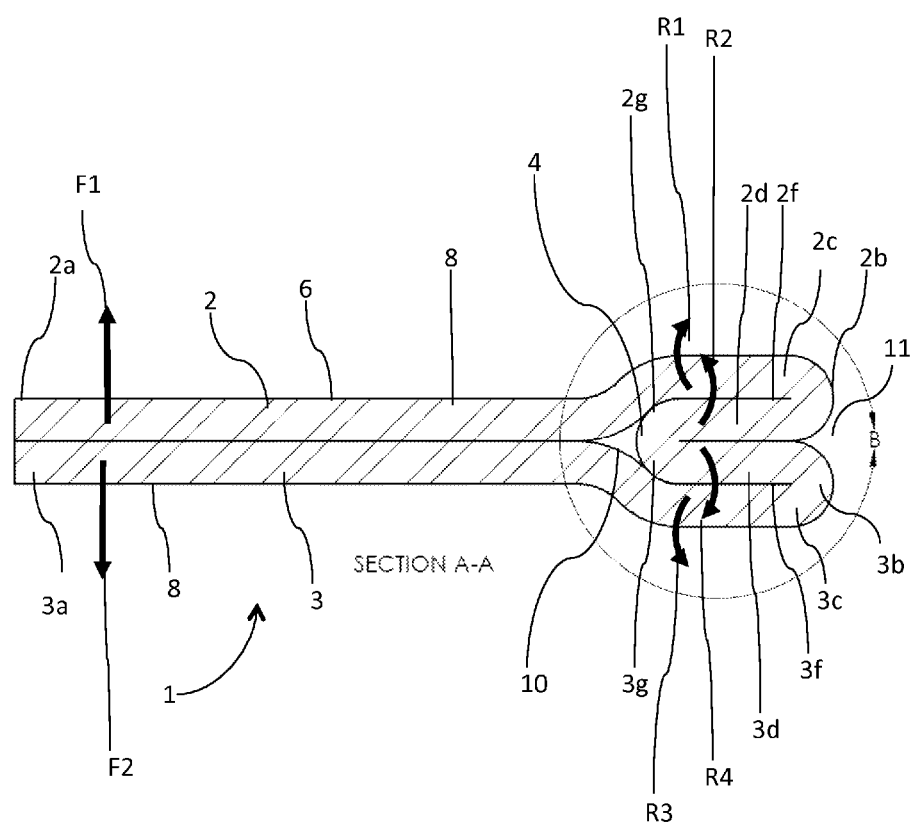
FIG. 4 illustrates a side cross sectional view of the embodiment of the transcend ligating clip along line A-A of FIG. 3.
Figure 5:
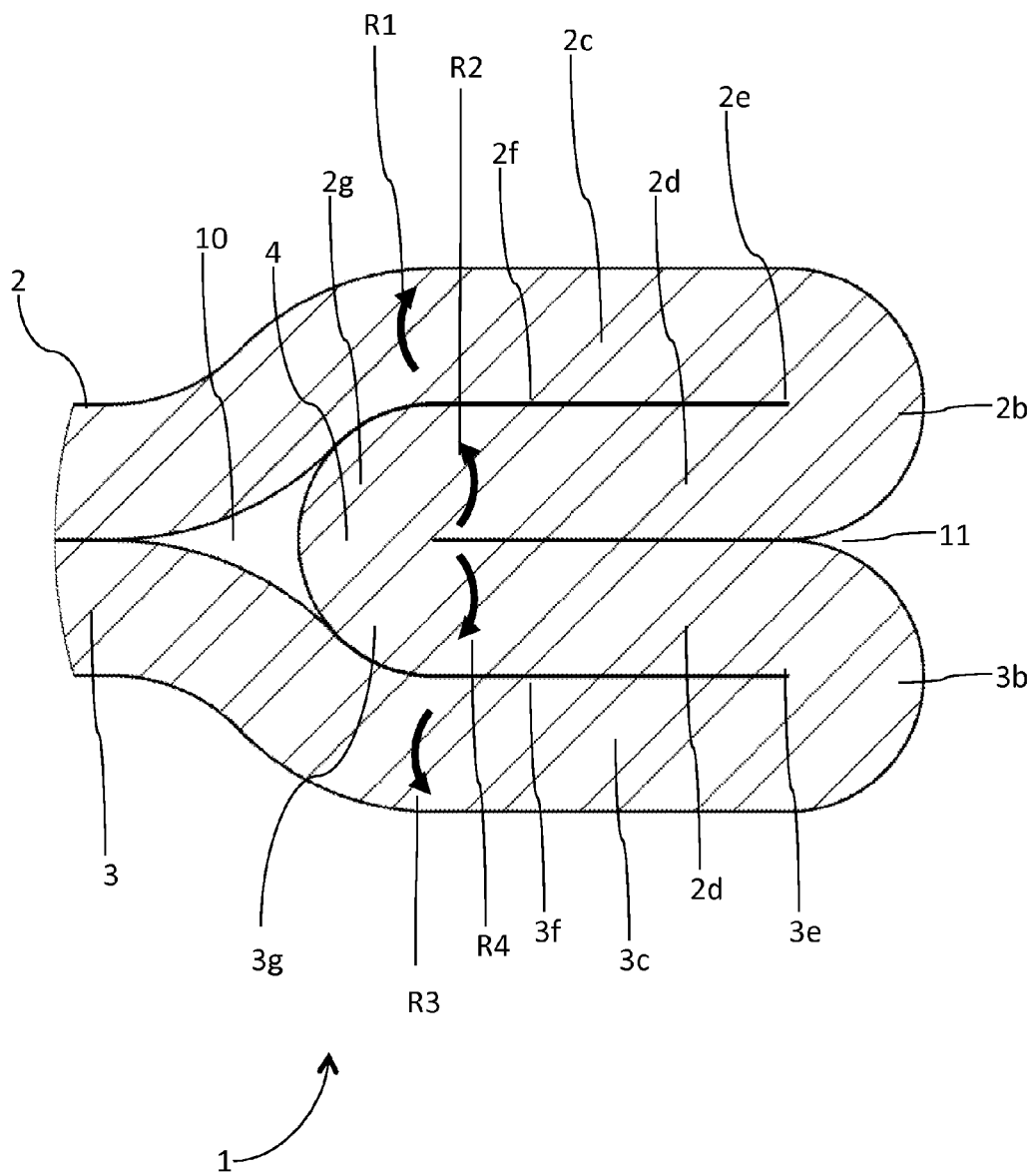
FIG. 5 illustrates an enlarged cross sectional side view of the embodiment of the transcend ligating clip along line B of FIG. 4.

FIG. 1 illustrates the ligating clip 1 in the open or uncompressed position. The ligating clip 1 will be in an open position before attachment or application over a blood vessel to ligate or occlude that vessel. FIGS. 2, 4, 6, and 7 illustrate the closed or compressed position of ligating clip 1 alone and clamped over a tubular vessel V.

The ligating clip 1 includes a pair of opposed elongated ligating legs 2 and 3, each having respective distal ends 2a and 3a, and respective proximal ends 2b and 3b. The distal ends 2a and 3a of ligating legs 2 and 3 are substantially parallel to one another and are relatively non-deformable.

The ligating leg 2 proximate to proximal end 2b extends in a outwardly lateral direction to form an external bending leg 2c. The external bending leg 2c curves in an inwardly lateral direction at proximal end 2b to form an internal bending leg 2d. The proximal end of 2b of external bending leg 2c and internal bending leg 2d curve towards each other, in an inwardly lateral direction, to form a first leg apex connection 2e. The first leg apex connection 2e is relatively deformable to allow clip 1 to compress from the open position to the closed position. A narrow channel 2f is formed between the external bending leg 2c and the internal bending leg 2d.

In further embodiments of the subject invention, the ligating leg 2 have may have variable cross-sectional widths from the distal end 2a to the external bending leg 2c to the proximal end 2b to internal bending leg 2d to the first leg apex connection 2e to minimize deflection of the clip 1 as it moves between the compressed and the uncompressed positions.

In other embodiments of the subject invention, the ligating leg 2 may have a continuous or variable cross-sectional shape from the distal end 2a to the external bending leg 2c to the proximal end 2b to internal bending leg 2d to the second leg apex connection 2e, wherein this shape may be selected from square, circular, elliptical, triangular, hexagonal, octagonal, or any suitable cross-sectional shape.

Ligating leg 2 contains an inner tissue contacting surface 5 and an outer surface 6 that both extend along the axis of ligating leg 2 in a substantially parallel direction.

The ligating leg 3 proximate to proximal end 3b extends in an outwardly lateral direction to form an external bending leg 3c. The external bending leg 3c curves in an inwardly lateral direction at proximal end 3b to form an internal bending leg 3d. The proximal end of 3b of external bending leg 3c and internal bending leg 3d curve towards each other, in an inwardly lateral direction, to form a second leg apex connection 3e. The second leg apex connection 3e is relatively deformable to allow clip 1 to compress from the open position to the closed position. A narrow channel 3f is formed between the external bending leg 3c and the internal bending leg 3d.

In further embodiments of the subject invention, ligating leg 3 have may have variable cross-sectional widths from the distal end 3a to the external bending leg 3c to the proximal end 3b to internal bending leg 3d to the second leg apex connection 3e to minimize deflection of the clip 1 as it moves between the compressed and the uncompressed positions.

In other embodiments of the subject invention, the ligating leg 3 may have a continuous or variable cross-sectional shape from the distal end 3a to the external bending leg 3c to the proximal end 3b to internal bending leg 3d to the second leg apex connection 3e, wherein this shape may be selected from square, circular, elliptical, triangular, hexagonal, octagonal, or any suitable cross-sectional shape.

Ligating leg 3 contains an inner tissue contacting surface 7 and an outer surface 8 that both extend along the axis of ligating leg 3 in a substantially parallel direction.

Ligating legs 2 and 3 are substantially mirror images of each other. Proximal end 2b is substantially a mirror image of proximal end 3b. External bending leg 2c is substantially a mirror image of external bending leg 3c. Internal bending leg 2d is substantially a mirror image of internal bending leg 3d. The first leg apex connection 2e is substantially a mirror image of second leg apex connection 3e. Narrow channel 2f is substantially a mirror image of narrow channel 3f.

Ligating legs 2 and 3 each have a contiguous cross-sectional configuration. This configuration is maintained as ligating legs 2 and 3 curve to form external bending legs 2c and 3c, and curve to form internal bending legs 2d and 3d, and then curve towards each other to form an apex connection 4.

Figure 7:
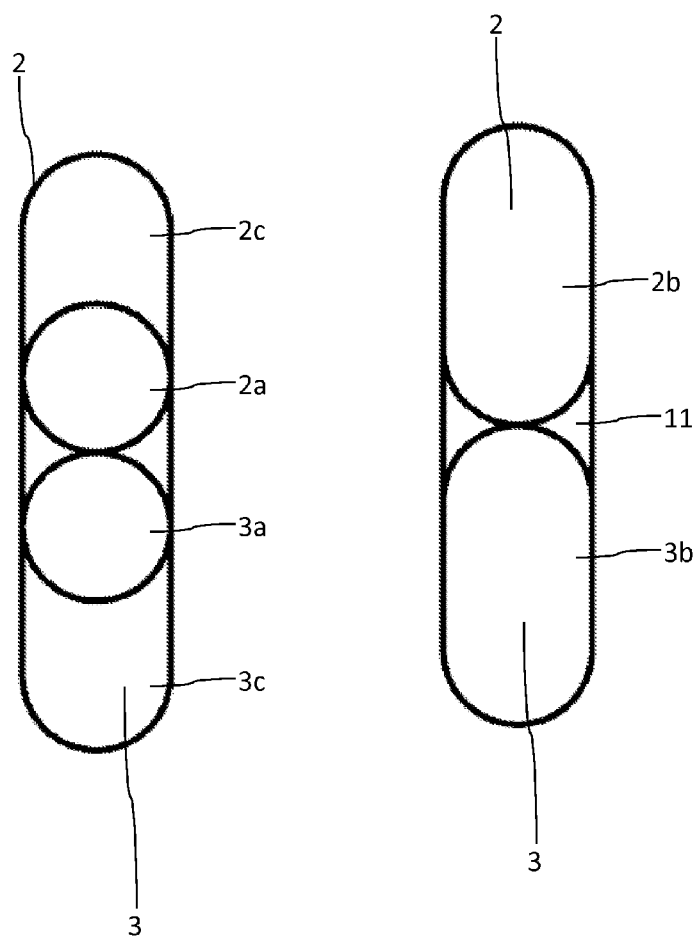
FIG. 7 illustrates a front view of the distal end and a front view of the proximal end of the embodiment of the transcend ligating clip.

FIG. 7 illustrates an enlarged cross-sectional view of ligating legs 2 and 3. Inner tissue contacting surface 5 and outer surface 6 form a cross-sectional configuration for ligating leg 2. Inner tissue contacting surface 7 and outer surface 8 form a cross-sectional configuration for ligating leg 3. Ligating legs 2 and 3 are substantially equivalent in size and shape. The cross-sectional size and shape of distal end 2a is substantially equivalent in size and shape to distal end 3a. The cross-sectional size and shape of external bending leg 2c is substantially equivalent in size and shape of external bending leg 3c. The cross-sectional size and shape of internal bending leg 2d is substantially equivalent in size and shape of internal bending leg 3d.

The distal ends 2g and 3g of the internal bending legs 2d and 3d curve towards each other, in an inwardly lateral direction, to form a clip apex connection 4. The distal, internal side of clip apex connection 4 forms within an internal movement space 10. Narrow channels 2f and 3f both end within internal movement space 10. The proximal, external side of clip apex connection 4 forms within an external movement space 11. The clip apex connection 4 is relatively deformable to allow the clip 1 to compress from the open position to the closed position within internal movement space 10 and an external movement space 11.

A clip applier with a jaws assembly (not shown) containing two opposing jaws legs, compresses and reduces the diameter of a tubular vessel V to be occluded or ligated with clip 1. This reduction in vessel V diameter prior placement of the clip 1, permits a vessel V with a much larger diameter than the distance between ligating legs 2 and 3 to be contained within clip 1.

The clip 1 is slid over compressed vessel V. As illustrated in FIG. 7, the vessel V is held between inner tissue contacting surface 5 of ligating leg 2 and inner tissue contacting surface 7 of ligating leg 3.

The compressed tubular vessel V, attempting to expand from its compressed position to an uncompressed position, applies outwardly lateral force F1 to inner tissue contacting surface 5 of ligating leg 2, and outwardly lateral force F2 to inner tissue contacting surface 7 of ligating leg 3. Outwardly lateral force F1 and outwardly lateral force F2 are substantially opposing forces.

Outwardly lateral force F1 on inner tissue contacting surface 5 of ligating leg 2 causes external bending leg 2c to rotate in direction R1 in a lateral direction away from internal bending leg 2d at the first leg apex connection 2e. In response to rotation R1, internal bending leg 2d begins to rotate in direction R2 in a lateral direction towards external bending leg 2c at apex 4. Rotation R2 substantially opposes rotation R1 to maintain the position of ligating leg 2 on the clip 1 over the compressed tubular V.

Outwardly lateral force F2 on inner tissue contacting surface 7 of ligating leg 3 causes external bending leg 3c to rotate in direction R3 in a lateral direction away from internal bending leg 3d at a first leg apex connection 3e.

Outwardly lateral force F2 on inner tissue contacting surface 5 of ligating leg 7 causes external bending leg 3c to rotate in direction R3 in a lateral direction away from internal bending leg 3d at the second leg apex connection 3e. In response to rotation R3, internal bending leg 3d begins to rotate in direction R4 in a lateral direction towards external bending leg 3c at apex 4. Rotation R4 substantially opposes rotation R3 to maintain the position of ligating leg 3 on the clip 1 over the compressed tubular vessel V Rotations R1 on external bending leg 2c and R3 on external bending leg 3c are substantially mirror images of each other. Rotations R2 on internal bending leg 2d and R4 on internal bending leg 3d are substantially mirror images of each other.

Rotations R2 and R4, oppose the rotations R1 and R3, respectively, caused by uncompressing forces F1 and F2 from the compressed vessel V, to maintain the substantially parallel position of ligating legs 2 and 3 over the compressed vessel V.

The vessel V will be remain occluded or ligated between the opposing inner tissue contacting surface 5 and the inner tissue contacting surface 7. The continuous outer surface of clip 1 will reduce irritation and trauma in tissue surrounding the ligated vessel V, since it does not have any sharp corners or edges that may pierce or cut surrounding tissue.

Figure 6:
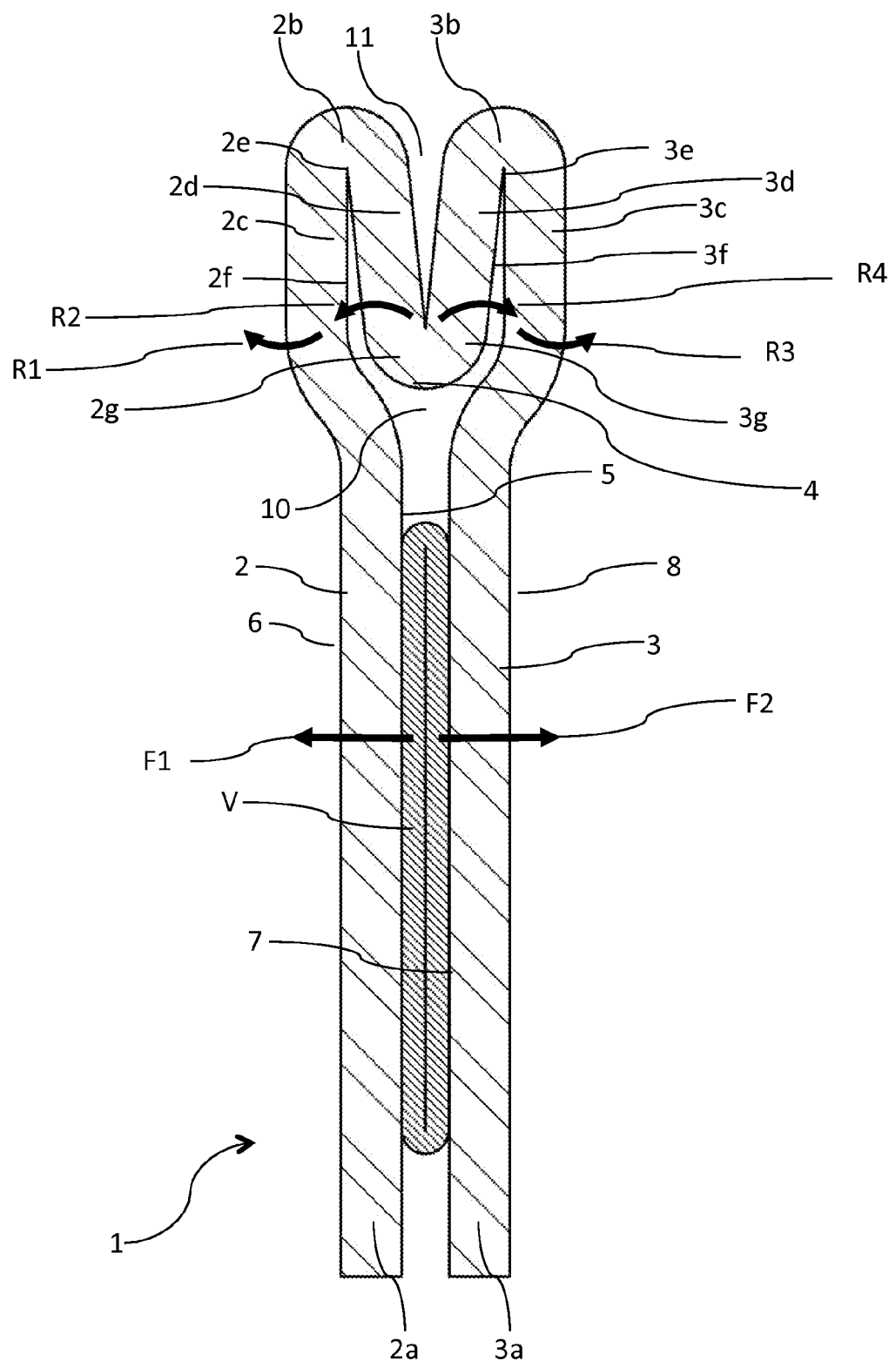
FIG. 6 illustrates a side cross sectioned view of the embodiment of the transcend ligating clip closed over a fully ligated and closed tubular vessel.

FIG. 6 illustrates the closed position of surgical vessel ligating clip 1 attached to vessel V. Ligating leg 3 is compressed over ligating leg 2. No internal fluid traverses vessel V when clip 1 is compressed over the vessel. The inner tissue contacting surfaces 5 and 7 promote ligation or occlusion of a tubular blood vessel without piercing or cutting the vessel. Once the surgical clip 1 is closed or compressed over a tubular vessel, the vessel tissue may gradually move or ooze into the spaces between inner tissue contacting surfaces 5 and 7 while remaining frictionally engaged such that the clip 1 does not move or become loose on the vessel.

In one embodiment of the subject invention, the clip 1 is 0.1 to 0.5 inches in length or width. In another embodiment of the subject invention, the clip is 0.25 inches in length. In a further embodiment of the subject invention, the clip 1 is intended to be used with a five millimeter trocar. In a further embodiment of the subject invention, the clip 1 is composed of titanium, stainless steel, tantalum, plastics materials, or a combination thereof. In an even further embodiment of the subject invention, the clip 1 is composed of biodegradable material.

What is claimed is:

1. A surgical clip, comprising:
   a relatively non-deformable first elongated external leg member extending along a first leg axis from a first proximal end to a first distal end,
   a relatively non-deformable first elongated internal leg member extending along the first leg axis from the first distal end to a first middle end,
   a relatively deformable first external apex member coupling the proximal end of the first elongated external leg member and the first elongated internal leg member whereby the first elongated external leg member and the first elongated internal leg member are substantially coplanar, further wherein the first elongated external leg member and the first elongated internal leg member have an external surface and an inner surface extending along the first leg axis, and have a cross-section transverse to the first leg axis and defined by a substantially curved boundary component;
   a relatively non-deformable second elongated external leg member extending along a second leg axis from a second proximal end to a second distal end,
   a relatively non-deformable second elongated internal leg member extending along the second external leg axis from the second distal end to a second middle end,
   a relatively deformable second external apex member coupling the proximal end of the second elongated external leg member and the second elongated internal leg member whereby the second elongated external leg member and the second elongated internal leg member are substantially coplanar, further wherein the second elongated external leg member and the second elongated internal leg member have an external surface extending and an inner surface along the second leg axis, and have a cross-section transverse to the second leg axis and defined by a substantially curved boundary component; and
   a relatively deformable internal apex member coupling the first middle end of the first elongated internal leg member with the second middle end of the second elongated internal leg member whereby the first leg axis and the second leg axis are substantially coplanar and substantially parallel and extend along a clip axis, whereby the first elongated internal leg member is opposite the first elongated internal leg member, further wherein the first elongated external leg member is opposite the second elongated external leg member;
   wherein the inner surface of the first elongated internal leg member contacts the inner surface of the second elongated internal leg member along an axis that is substantially parallel to the first leg axis and the second leg axis when the surgical clip is in a closed position.

2. A surgical clip according to claim 1, wherein any uncompressing forces applied to the inner lateral surfaces of first elongated external leg member and the second elongated external leg member will cause a first rotation of the first elongated external leg member at the first external apex away from the first elongated internal leg member and the clip axis, and a second rotation of the second elongated external leg member at the second external apex away from the second elongated internal leg member and the clip axis, wherein the first elongated internal leg member applies a third rotation at the internal apex member, wherein the third rotation substantially opposes the first rotation, wherein the second elongated internal leg member applies a fourth rotation at the internal apex member, wherein the fourth rotation substantially opposes the second rotation.

3. A surgical clip according to claim 1, wherein the third rotation substantially opposes the first rotation, and the fourth rotation substantially opposes the second rotation to substantially maintain the first and second elongated external leg members in a substantially parallel position with each other.

4. A surgical clip according to claim 1, wherein the first external leg member and second external leg member each comprise substantially variable widths transverse to the respective first leg axis and second leg axis.

5. A surgical clip according to claim 1, wherein the first external leg member and second external leg member each comprise substantially variable shapes transverse to the respective first leg axis and second leg axis.

6. A surgical clip according to claim 1, wherein respective first leg member and second leg member each comprise a substantially uniform width transverse to the respective first leg axis and second leg axis.

7. A surgical clip according to claim 1, wherein the first leg axis and the second leg axis are substantially parallel, and substantially parallel to the clip axis.

8. A surgical clip according to claim 1, wherein the first external leg member, the first internal leg member, the second external leg member, and the second internal leg member each comprise a substantially non-textured external surface and inner surface.

9. A surgical clip according to claim 1, wherein the surgical clip comprises one piece.

10. A surgical clip according to claim 1, wherein the surgical clip comprises 0.1 to 0.5 inches in length.

11. A surgical clip according to claim 1, wherein the surgical clip comprises titanium or stainless steel.

12. A surgical clip according to claim 1, wherein the surgical clip comprises biodegradable material.

13. A surgical clip according to claim 1, wherein there is no minimum vessel closure diameter for the surgical clip.

14. A surgical clip according to claim 1, wherein the surgical clip comprises a substantially Y-shaped configuration.

* * * * *